(12) United States Patent
Berube et al.

(10) Patent No.: US 6,312,427 B1
(45) Date of Patent: Nov. 6, 2001

(54) DIRECTIONAL REFLECTOR SHIELD ASSEMBLY FOR A MICROWAVE ABLATION INSTRUMENT

(75) Inventors: Dany Berube, Fremont; Robert E. Woodard, Hayward; Theodore C. Ormsby, Milpitas, all of CA (US)

(73) Assignee: AFx, Inc., Fremont, CA (US)

( * ) Notice: Subject to any disclaimer, the term of this patent is extended or adjusted under 35 U.S.C. 154(b) by 0 days.

(21) Appl. No.: 09/496,477

(22) Filed: Feb. 2, 2000

Related U.S. Application Data

(62) Division of application No. 09/178,066, filed on Oct. 23, 1998.

(51) Int. Cl.$^7$ .................................................. A61B 18/04
(52) U.S. Cl. ........................... 606/33; 607/101; 607/156
(58) Field of Search ................................ 607/154, 155, 607/156, 122, 101; 606/33, 34, 41, 46; 600/11, 13

(56) References Cited

U.S. PATENT DOCUMENTS

| 4,204,549 | 5/1980 | Paglione . |
| 4,601,296 | * 7/1986 | Yerushalmi ........................... 607/156 |
| 4,641,649 | 2/1987 | Walinsky et al. . |
| 4,823,812 | * 4/1989 | Eshel et al. ........................... 607/156 |
| 5,129,396 | 7/1992 | Rosen et al. . |
| 5,246,438 | 9/1993 | Langberg . |
| 5,405,346 | 4/1995 | Grundy et al. . |
| 5,800,494 | 9/1998 | Campbell et al. . |
| 5,971,983 | 10/1999 | Lesh . |
| 6,004,269 | 12/1999 | Crowley et al. . |
| 6,027,497 | 2/2000 | Daniel et al. . |
| 6,086,583 | 7/2000 | Ouchi . |
| 6,161,543 | 12/2000 | Cox et al. . |
| 6,171,303 | 1/2001 | Ben-Haim et al. . |

FOREIGN PATENT DOCUMENTS

| 0048402A1 | 3/1982 | (EP) . |
| 0139609A1 | 5/1985 | (EP) . |
| 0248758A1 | 12/1985 | (EP) . |

* cited by examiner

Primary Examiner—Linda C. M. Dvorak
Assistant Examiner—David Ruddy
(74) Attorney, Agent, or Firm—Beyer Weaver & Thomas

(57) ABSTRACT

A directional reflective shield assembly (25) is provided for a microwave ablation instrument (20) having an antenna (23) coupled to a transmission line (21). The antenna (23) is formed to generate an electric field sufficiently strong to cause tissue ablation. The shield assembly (25) includes a cradle device (26) disposed about the antenna (23) in a manner substantially shielding a surrounding area of the antenna (23) from the electric field radially generated therefrom. The cradle device (26) further provides a window portion (27) communicating with the antenna (23) which is strategically located relative the antenna to direct a majority of the field generally in a predetermined direction.

29 Claims, 3 Drawing Sheets

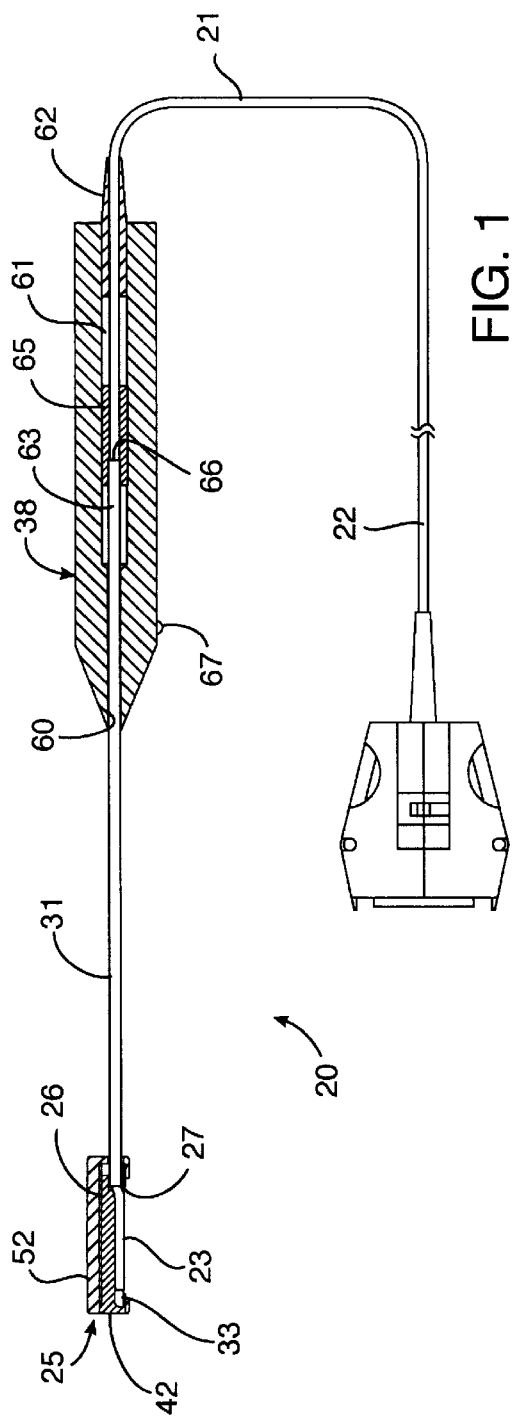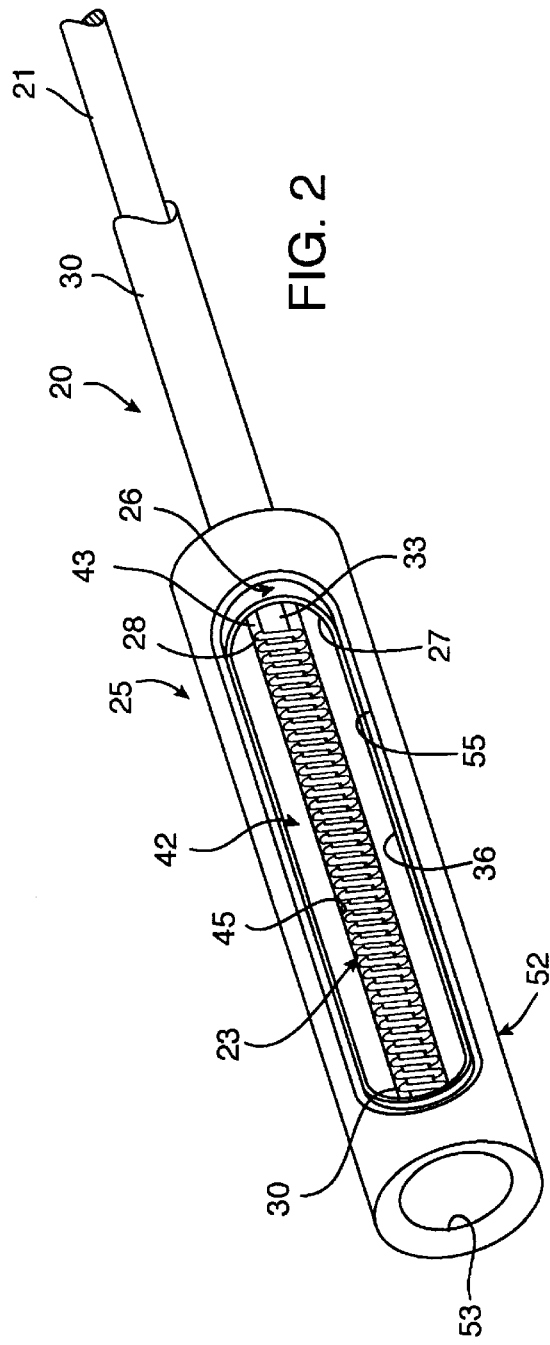

DIRECTIONAL REFLECTOR SHIELD ASSEMBLY FOR A MICROWAVE ABLATION INSTRUMENT

This application is a division of 09/178,066 filed Oct. 23, 1998.

BACKGROUND OF THE INVENTION

1. Field of Invention

The present invention relates, generally, to ablation instrument systems that use electromagnetic energy in the microwave frequencies to ablate internal bodily tissues, and, more particularly, to antenna arrangements and instrument construction techniques that direct the microwave energy in selected directions that are relatively closely contained along the antenna.

2. Description of the Prior Art

It is well documented that atrial fibrillation, either alone or as a consequence of other cardiac disease, continues to persist as the most common cardiac arrhythmia. According to recent estimates, more than one million people in the U.S. suffer from this common arrhythmia, roughly 0.15% to 1.0% of the population. Moreover, the prevalence of this cardiac disease increases with age, affecting nearly 8% to 17% of those over 60 years of age.

Although atrial fibrillation may occur alone, this arrhythmia often associates with numerous cardiovascular conditions, including congestive heart failure, hypertensive cardiovascular disease, myocardial infarcation, rheumatic heart disease, and stroke. Regardless, three separate detrimental sequelae result: (1) a change in the ventricular response, including the onset of an irregular ventricular rhythm and an increase in ventricular rate; (2) detrimental hemodynamic consequences resulting from loss of atroventricular synchrony, decreased ventricular filling time, and possible atrioventricular valve regurgitation; and (3) an increased likelihood of sustaining a thromboembolic event because of loss of effective contraction and atrial stasis of blood in the left atrium.

Atrial arrhythmia may be treated using several methods. Pharmacological treatment of atrial fibrillation, for example, is initially the preferred approach, first to maintain normal sinus rhythm, or secondly to decrease the ventricular response rate. While these medications may reduce the risk of thrombus collecting in the atrial appendages if the atrial fibrillation can be converted to sinus rhythm, this form of treatment is not always effective. Patients with continued atrial fibrillation and only ventricular rate control continue to suffer from irregular heartbeats and from the effects of impaired hemodynamics due to the lack of normal sequential atrioventricular contractions, as well as continue to face a significant risk of thromboembolism.

Other forms of treatment include chemical cardioversion to normal sinus rhythm, electrical cardioversion, and RF catheter ablation of selected areas determined by mapping. In the more recent past, other surgical procedures have been developed for atrial fibrillation, including left atrial isolation, transvenous catheter or cryosurgical ablation of His bundle, and the Corridor procedure, which have effectively eliminated irregular ventricular rhythm. However, these procedures have for the most part failed to restore normal cardiac hemodynamics, or alleviate the patient's vulnerability to thromboembolism because the atria are allowed to continue to fibrillate. Accordingly, a more effective surgical treatment was required to cure medically refractory atrial fibrillation of the heart.

On the basis of electrophysiologic mapping of the atria and identification of macroreentrant circuits, a surgical approach was developed which effectively creates an electrical maze in the atrium (i.e., the MAZE procedure) and precludes the ability of the atria to fibrillate. Briefly, in the procedure commonly referred to as the MAZE III procedure, strategic atrial incisions are performed to prevent atrial reentry and allow sinus impulses to activate the entire atrial myocardium, thereby preserving atrial transport function postoperatively. Since atrial fibrillation is characterized by the presence of multiple macroreentrant circuits that are fleeting in nature and can occur anywhere in the atria, it is prudent to interrupt all of the potential pathways for atrial macroreentrant circuits. These circuits, incidentally, have been identified by intraoperative mapping both experimentally and clinically in patients.

Generally, this procedure includes the excision of both atrial appendages, and the electrical isolation of the pulmonary veins. Further, strategically placed atrial incisions not only interrupt the conduction routes of the common reentrant circuits, but they also direct the sinus impulse from the sinoatrial node to the atrioventricular node along a specified route. In essence, the entire atrial myocardium, with the exception of the atrial appendages and the pulmonary veins, is electrically activated by providing for multiple blind alleys off the main conduction route between the sinoatrial node to the atrioventricular node. Atrial transport function is thus preserved postoperatively as generally set forth in the series of articles: Cox, Schuessler, Boineau, Canavan, Cain, Lindsay, Stone, Smith, Corr, Change, and D'Agostino, Jr., *The Surgical Treatment Atrial Fibrillation* (pts. 1–4), 101 THORAC CARDIOVASC SURG., 402–426, 569–592 (1991).

While this MAZE III procedure has proven effective in ablating medically refractory atrial fibrillation and associated detrimental sequelae, this operational procedure is traumatic to the patient since substantial incisions are introduced into the interior chambers of the heart. Consequently, other techniques have thus been developed to interrupt and redirect the conduction routes without requiring substantial atrial incisions. One such technique is strategic ablation of the atrial tissues through ablation catheters.

Most approved ablation catheter systems now utilize radio frequency (RF) energy as the ablating energy source. Accordingly, a variety of RF based catheters and power supplies are currently available to electrophysiologists. However, radio frequency energy has several limitations including the rapid dissipation of energy in surface tissues resulting in shallow "burns" and failure to access deeper arrhythmic tissues. Another limitation of RF ablation catheters is the risk of clot formation on the energy emitting electrodes. Such clots have an associated danger of causing potentially lethal strokes in the event that a clot is dislodged from the catheter.

As such, catheters which utilize electromagnetic energy in the microwave frequency range as the ablation energy source are currently being developed. Microwave frequency energy has long been recognized as an effective energy source for heating biological tissues and has seen use in such hyperthermia applications as cancer treatment and preheating of blood prior to infusions. Accordingly, in view of the drawbacks of the traditional catheter ablation techniques, there has recently been a great deal of interest in using microwave energy as an ablation energy source. The advantage of microwave energy is that it is much easier to control and safer than direct current applications and it is capable of generating substantially larger lesions than RF catheters, which greatly simplifies the actual ablation procedures.

Typical of such microwave ablation systems are described in the U.S. Pat. No. 4,641,649 to Walinsky; U.S. Pat. No. 5,246,438 to Langberg; U.S. Pat. No. 5,405,346 to Grundy, et al.; and U.S. Pat. No. 5,314,466 to Stern, et al, each of which is incorporated herein by reference.

Most of the existing microwave ablation catheters contemplate the use of longitudinally extending helical antenna coils that direct the electromagnetic energy in a radial direction that is generally perpendicular to the longitudinal axis of the catheter although the fields created are not well constrained to the antenna itself. Although such catheter designs work well for a number of applications, such radial output, while controlled, is inappropriate for use in MAZE III procedures for example which require very strategically positioned and formed lesions. Thus, it would be desirable to provide microwave ablation catheter designs that are capable of effectively transmitting electromagnetic energy that more closely approximates the length of the antenna, and in a specific direction, such as generally perpendicular to the longitudinal axis of the catheter but constrained to a selected radial region of the antenna.

SUMMARY OF THE INVENTION

To achieve the foregoing and other objects and in accordance with the purpose of the present invention, a variety of improved ablation instruments and particularly microwave ablation instruments are disclosed. In some embodiments, a directional reflective shield assembly is provided for a microwave ablation instrument having an antenna coupled to a transmission line. The antenna is formed to generate an electric field sufficiently strong to cause tissue ablation. The shield includes a cradle device disposed about the antenna in a manner substantially shielding a surrounding area of the antenna from the electric field radially generated therefrom. The cradle device further provides a window portion communicating with the antenna which is strategically located relative the antenna to direct a majority of the field generally in a predetermined direction.

In one embodiment, an insert device is disposed in a cavity of the cradle. The insert device provides a recess formed and dimensioned for receipt of the antenna therein in a manner substantially isolating the antenna from direct contact with the cradle device. The insert device further includes a directional port extending into the recess and aligned to communicate with the window portion of the cradle device to direct the majority of the field generally in the redetermined direction.

Another embodiment includes an insulator in conductive contact with the cradle device to transfer heat therefrom. The insulator is preferably disposed about the cradle member, and includes a longitudinally extending bore formed and dimensioned for sliding receipt of the cradle device therein. A directional window extends into the bore and is aligned to communicate with the window portion of the cradle device and the directional port of the insert device to direct the majority of the field generally in the predetermined direction.

In still another embodiment, a microwave ablation instrument includes a transmission line having a proximal portion suitable for connection to an electromagnetic energy source, and an antenna coupled to the transmission line for radially generating an electric field sufficiently strong to cause tissue ablation. A shield assembly is coupled to the antenna to substantially shield a surrounding area of the antenna from the electric field radially generated therefrom while permitting a majority of the field to be directed generally in a predetermined direction.

In yet another embodiment, a microwave ablation instrument includes a bendable, malleable tubular shaft having a proximal portion and a distal portion, and a transmission line disposed within the tubular shaft. The transmission line includes a proximal portion suitable for connection to an electromagnetic energy source. An antenna is supported by the distal portion of the tubular shaft, and is coupled to the transmission line for radially generating an electric field sufficiently strong to cause tissue ablation. A microwave absorbent is disposed peripherally around the proximal portion of the tubular shaft to substantially absorb residual microwave radiation transmitted by the proximal portion thereof.

In one embodiment, a handle is provided which is mounted to the proximal portion of the tubular shaft. The handle includes an interior wall defining a cavity portion formed and dimensioned for termination of the tubular shaft proximal portion terminates therein. A material containing a silicon based microwave absorbent is disposed about the proximal portion and the transmission line in the cavity.

BRIEF DESCRIPTION OF THE DRAWINGS

The assembly of the present invention has other objects and features of advantage which will be more readily apparent from the following description of the best mode of carrying out the invention and the appended claims, when taken in conjunction with the accompanying drawing, in which:

FIG. 1 is a diagrammatic top plan view, in cross-section, of a microwave ablation instrument system with a directional reflective shield assembly constructed in accordance with one embodiment of the present invention.

FIG. 2 is an enlarged, fragmentary, top perspective view of the shield assembly of FIG. 1 mounted to an antenna assembly of the ablation instrument system.

DETAILED DESCRIPTION OF THE INVENTION

Figure 3:
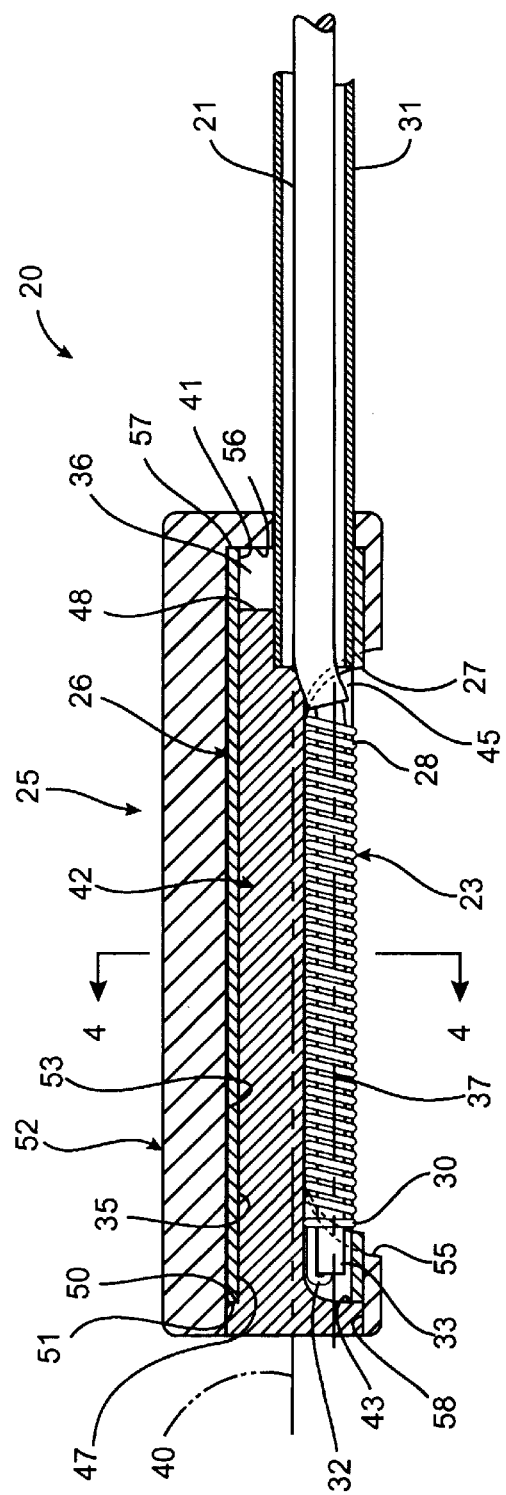
FIG. 3 is a side elevation view, in cross-section, of the shield assembly of FIG. 2.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various FIGURES.

Turning now to FIGS. 1 and 2, a microwave ablation instrument, generally designated 20, is provided which includes a transmission line 21 having a proximal portion 22 suitable for connection to an electromagnetic energy source (not shown), and an antenna 23 coupled to the transmission line 21 for radially generating an electric field sufficiently strong to cause tissue ablation. A shield assembly, generally designated 25, is coupled to the antenna 23 to substantially shield a peripheral area immediately surrounding the antenna from the electric field radially generated therefrom while permitting a majority of the field to be directed generally in a predetermined direction.

More specifically, a directional reflective shield assembly 25 is provided for a microwave ablation instrument including a cradle device 26 disposed about the antenna 23 in a manner substantially shielding a surrounding area of the antenna from the electric field radially generated therefrom. The cradle device 26 further provides a window portion 27 communicating with the antenna 23 which is strategically located relative the antenna to direct a majority of the field generally in a predetermined direction.

Accordingly, the shield assembly of the present invention enables predetermined directional transmission of the electric field regardless of the radial transmission pattern of the antenna. Tissue ablation can thus be more strategically controlled, directed and performed without concern for undesirable ablation of other adjacent tissues which may otherwise be within the electromagnetic ablation range radially emanating from the antenna. In other words, any other tissues surrounding the peripheral sides of the antenna which are out of line of the window portion of the cradle will not be subjected to the directed electric field and thus not be ablated. This ablation instrument assembly is particularly suitable for ablation procedures requiring accurate tissue ablations such as those required in the MAZE III procedure above-mentioned.

It will be appreciated that the phrase "peripheral area immediately surrounding the antenna" is defined as the immediate radial transmission pattern of the antenna which is within the electromagnetic ablation range thereof when the shield assembly is absent.

Transmission line 21, which is supported within a tubular shaft 31, is typically coaxial, and coupled to a power supply (not shown) which is external to instrument 20. As best illustrated in FIGS. 2 and 3, the microwave ablation instrument 20 generally includes an antenna 23 with a proximal end 28 and a distal end 30. The proximal end 28 of antenna 23 is grounded to an outer conductor (not shown) of transmission line 21. The distal end 30 of antenna 23 is attached to center conductor 32 of transmission line 21. Typically, antenna 23 is helical or in the form of a coil, i.e. an antenna coil, which is made from any suitable material, such as spring steel, beryllium copper, or silver-plated copper. However, the antenna may be any other configuration, such as a monopole, which radiates a cylindrical pattern consistent with the length thereof The connection between the antenna 23 and center conductor 32 may be made in any suitable manner such as soldering, brazing, ultrasonic welding or adhesive bonding. In other embodiments, the antenna 23 can be wound from the center conductor of the transmission line itself. This is more difficult from a manufacturing standpoint but has the advantage of forming a more rugged connection between the antenna and center conductor.

The outer diameter of antenna coil 23 will vary to some extent based on the particular application of the instrument. By way of example, a instrument suitable for use in an atrial fibrillation application may have typical coil outer diameters in the range of approximately 0.07 to 0.10 inches. More preferably, the outer diameter of antenna coil 23 may be in the range of approximately 0.08 to 0.09 inches.

The actual number of turns of the antenna coil may vary a great deal in accordance with the needs of a particular system. Some of the factors that will dictate the number of turns used include the coil diameter and pitch, the desired length of the lesion, the antenna configuration, the instrument diameter, the frequency of the electromagnetic energy, the desired field strength and the match within the tissue. Moreover, since these coiled antennas are preferably filled or cast with a silicone insulator to insulate each coil from one another and from the center conductor, the pitch of the coils can be smaller and the number of turns increased. In MAZE III applications, for example, the antenna is comprised of about thirty-seven (37) turns, and has a length in the range of approximately 19.8 mm to 20.0 mm. The antenna is typically spaced at least 0.5 mm, as for example in the range of approximately 0.5 to 2.0 mm, from the distal end of the transmission line shield (not shown) and at least approximately 0.5 mm, as for example in the range of approximately 0.5 to 1.0 mm from the distal end of the transmission line dielectric 33.

To substantially reduce or eliminate electromagnetic radiance of the distal end of the transmission line 21, the antenna is fed at its resonance frequency to better define the electromagnetic field along the coil. The antenna is preferably tuned by adjusting the length and the number of turns of the coil so that the resonance frequency of the radiative structure is in the range of about 2.45 GHz, for example. Consequently, the energy delivery efficiency of the antenna is increased, while the reflected microwave power is decreased which in turn reduces the operating temperature of the transmission line. Moreover, the radiated electromagnetic field is substantially constrained from the proximal end to the distal end of the antenna. Thus, when a longitudinally extending coil is used, the field extends substantially radially perpendicularly to the antenna and is fairly well constrained to the length of the antenna itself regardless of the power used. This arrangement serves to provide better control during ablation. Instruments having specified ablation characteristics can be fabricated by building instruments with different length antennas.

Briefly, the power supply (not shown) includes a microwave generator which may take any conventional form. When using microwave energy for tissue ablation, the optimal frequencies are generally in the neighborhood of the optimal frequency for heating water. By way of example, frequencies in the range of approximately 800 MHz to 6 GHz work well. Currently, the frequencies that are approved by the U.S. Food and Drug Administration for experimental clinical work are 915 MHz and 2.45 GHz. Therefore, a power supply having the capacity to generate microwave energy at frequencies in the neighborhood of 2.45 GHz may be chosen. At the time of this writing, solid state microwave generators in the 1–3 GHz range are very expensive. Therefore, a conventional magnetron of the type commonly used in microwave ovens is utilized as the generator. It should be appreciated, however, that any other suitable microwave power source could be substituted in its place, and that the explained concepts may be applied at other frequencies like about 434 MHz, 915 MHz or 5.8 GHz (ISM band).

Referring back to FIGS. 2 and 3, the shield assembly of the present invention will be described in detail. In accordance with the present invention, cradle device 26 defines a window portion 27 strategically sized and located to direct a majority of the electromagnetic field generally in a predetermined direction. Cradle device 26 is preferably tubular or cylindrical-shell shaped having an interior wall 35 defining a cavity 36 extending therethrough which is formed for receipt of the antenna 23 therein. While the cradle device is shown and described as substantially cylindrical-shaped along the longitudinal and cross-section dimensions, it will be appreciated that a plurality of forms may be provided to accommodate different antenna shapes or to conform to other external factors necessary to complete a surgical procedure. For example, by longitudinally curving the antenna, either through manual bending or through manufacture, a curvilinear ablative pattern may be achieved. Such a configuration, by way of example, may be necessary when ablating tissue around the pulmonary veins in the MAZE III procedure.

Cradle device 26 is preferably thin walled to minimize weight addition to the shield assembly, while being sufficiently thick to achieve the appropriate microwave shielding as well as provide the proper mechanical rigidity to the antenna area. In the preferred embodiment, cradle device 26 is composed of a conductive, metallic material which inherently functions as a reflector. The walls of the cradle device, therefore, are substantially impenetrable to the passage of microwaves emanating from the antenna. Moreover, a percentage of microwaves may be reflected them back into the cavity 36, and subsequently remitted out of window portion 27. One particularly suitable material is stainless steel, for example, having a thickness in the range of about 0.010 inches to about 0.025 inches, and more preferably about 0.015 inches.

As mentioned, an elongated helical microwave antenna normally emits an electromagnetic field substantially radially perpendicular to the antenna length which is fairly well constrained to the length of the coil regardless of the power used. Accordingly, the proximal and distal ends of the cradle may not require shielding by the cradle device in the same manner as that required radially perpendicular to the longitudinal axis of the antenna.

Figure 4:
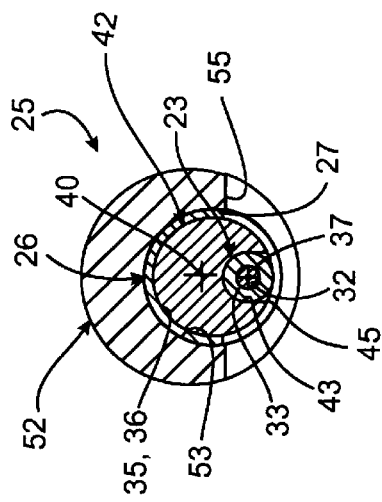
FIG. 4 is a front elevation view of the shield assembly taken substantially along the plane of the line 4—4 in FIG. 3.
Figure 5:
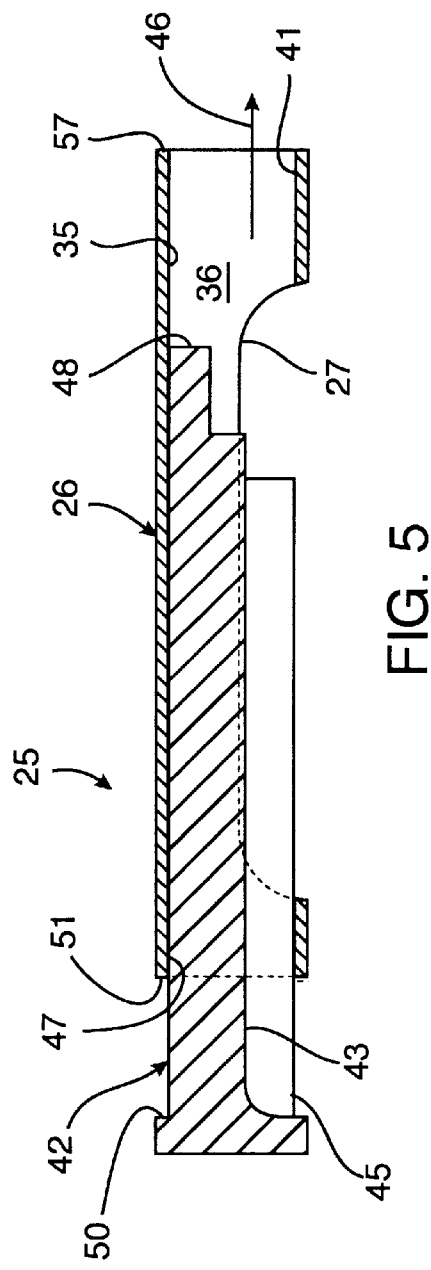
FIG. 5 is an exploded, side elevation view, in cross-section, of the shield assembly of FIG. 2, illustrating sliding receipt of an insert device in a cradle device of the shield assembly.

As best viewed in FIGS. 4 and 5, window portion 27 preferably radially extends through one side of the cradle and into the cavity 36, and further extends longitudinally along cradle in a direction substantially parallel to the longitudinal axis thereof. The length of the ablative radiation is therefore generally constrained to the length of the coil, and may be adjusted by either adjusting the length of the antenna (a helical antenna for example), or by adjusting the longitudinal length of the window portion 27. To maximize efficiency, however, the length of the window portion 27 is generally a little longer than the longitudinal length of the antenna 23, by about 1–2 mm on each side. This allows reflections out of the Window portion. It will be appreciated, however, that the window portion may be collectively defined by a plurality of sections (not shown), or that the cradle device may include more than one strategically positioned window portion.

For a tubular cradle device 26, FIG. 4 illustrates that the circumferential opening of the window portion 27 may extend circumferentially from about 45° to about 180°, and most preferably extend circumferentially about 160°. A substantial portion of the backside of the antenna, therefore, is shielded from ablative exposure of the microwaves radially generated by the antenna in directions substantially perpendicular to the longitudinal axis 37 thereof. The circumferential dimension of window portion 27, hence, may vary according to the breadth of the desired ablative exposure without departing from the true spirit and nature of the present invention.

Accordingly, the predetermined direction of the ablative electromagnetic field radially generated from the antenna may be substantially controlled by the circumferential opening dimension, the length and the shape of the cradle window portion 27. Manipulating the positioning of window portion 27 in the desired direction, thus, controls the direction of the tissue ablation without subjecting the remaining peripheral area immediately surrounding the antenna to the ablative electromagnetic field.

Briefly, ablation instrument 20 includes a handle 38 coupled to the antenna and the cradle device 26 through an elongated tubular shaft 31. By manually manipulating the handle, the cradle window portion 27 may be oriented and positioned to perform the desired ablation. The shaft is preferably provided by a metallic hypotube which is mounted to the metallic cradle device through brazing paste, welding or the like. Moreover, the shaft 31 is preferably bendable and malleable in nature to enable shape reconfiguration to position the antenna and the cradle device at a desired orientation relative the handle. This enables the surgeon to appropriately angle the window portion toward the targeted region for tissue ablation. It will be appreciated, however, that the material of the shaft is further sufficiently rigid so that the shaft is not easily deformed during operative use. Such materials, for example, includes stainless steel or aluminum having diameters ranging from about 0.090 inches to about 0.200 inches with wall thickness ranging from about 0.050 inches to about 0.025 inches. Most preferably, the shaft is 304 stainless steel having an outer diameter of about 0.120 inches and a wall thickness of about 0.013 inches.

The resonance frequency of the antenna is preferably tuned assuming contact between the targeted tissue and the longitudinal dimension of the antenna 23 exposed by the window portion 27. Hence, should a portion of, or substantially all of, the exposed region of the antenna not be in contact with the targeted tissue during ablation, the resonance frequency will be adversely changed and the antenna will be untuned. As a result, the portion of the antenna not in contact with the targeted tissue will radiate the electromagnetic radiation into the surrounding air. The efficiency of the energy delivery into the tissue will consequently decrease which in turn causes the penetration depth of the lesion to decrease.

Thus, tissue contact with the antenna is best achieved placing and orienting the antenna longitudinally adjacent and into the cradle window portion 27, as viewed in FIGS. 3 and 4. The longitudinal axis 37 of the antenna is thus off-set from, but parallel to, the longitudinal axis 40 of cradle device 26 in a direction toward the window portion. In this regard, the antenna may generally be positioned closer to the area designated for tissue ablation. Moreover, by positioning the antenna actively in the window portion 27 of the cradle device, the transmissive power of the antenna may be effected substantially along the full circumferential opening of the window portion 27.

This arrangement of positioning the antenna actively in the cradle window portion 27 is partially achieved by mounting a distal portion of shaft 31 in alignment with the window portion, and to an interior wall 35 of cradle device 26. As shown in FIG. 3, the distal end of the shaft 31 extends through a proximal opening 41 into cavity 36 of the cradle device 26 which initially positions the longitudinal axis of the shaft and that of the cradle device substantially parallel one another. It will be appreciated, however, that these axes need not be parallel.

To maintain the electromagnetic field characteristics of the antenna during operative use, it is imperative to stabilize the position of antenna 23 relative the cradle device 26. Relative position changes or antenna deformation may alter the resonant frequency of the antenna, which in turn, changes the field characteristics of the antenna. Accordingly, to stabilize the antenna 23 relative the cradle device 26, the shield assembly 25 further includes an insert device, generally designated 42, disposed in cradle device cavity 36 between the cradle device and the antenna.

Insert device 42 includes a longitudinally extending recess 43 formed and dimensioned for press-fit receipt of the antenna therein. In accordance with the present invention, the recess 43 is preferably cylindrical shaped and extends substantially longitudinally along a surface of the insert device. This configuration positions, stabilizes and retains the helical antenna 23 actively in the window portion 27 to maximize exposure of the targeted tissue to the microwaves generated by antenna. The recess 43 further includes a directional port 45 communicating with the recess 43 which aligns the same with the window portion 27 of the cradle device 26 to direct the majority of the field generally in the predetermined direction. For a curvilinear antenna, it will be understood that the recess may be similarly conformed.

The insert device 42 further performs the function of decreasing the coupling between the antenna 23 and the metallic cradle device 26. Should the antenna be too close to the metallic surface of the cradle device, a strong current may be induced at the surface thereof. This surface current will increase the resistive losses in the metal and the temperature of the cradle device will increase. On the other hand, direct conductive contact or substantially close contact of the antenna with the metallic cradle device will cause the reflective cradle device to become part of the radiative structure, and begin emitting electromagnetic energy in all directions.

Insert device 42 is therefore preferably provided by a good dielectric material which is relatively unaffected by microwave exposure, and thus capable of transmission of the electromagnetic field therethrough. Preferably, this material is provided by a low-loss dielectric material such as TEFLON, silicone, or polyethylene, polyimide, etc.

Insert device 42 is preferably provided by a substantially solid cylindrical structure dimensioned for a sliding interference fit, in the direction of arrow 46 (FIG. 5), through a distal opening 47 of the cradle device cavity 36. Thus, the outer diameter of the insert device is preferably slightly larger than the inner diameter of the cavity 36 defined by cradle interior wall 35. A proximal portion of insert device 42 includes a semicircular alignment tongue 48 formed to cooperate with the distal end of the shaft 31 during sliding receipt of the insert device 42 in the cradle device 26 for alignment thereof. Moreover, a distal portion of the insert device 42 includes an annular shoulder portion 50 formed and dimensioned to contact a distal edge 51 of cradle device 26 upon full insertion of insert device into cavity 36. Collectively, the alignment tongue 48 and the annular shoulder portion 50 cooperate to properly align the recess 43 and the directional port 45, and thus the press-fit antenna 23, in the window portion 27 of the cradle device. Moreover, for reasons to be discussed henceforth, the circumferential dimension of the shoulder portion 50 is conformed substantially similar to that of the cradle device (FIG. 3).

By composing the cradle device 26 of a high conductivity metal, a superior microwave reflector is produced. Thus, when an electromagnetic wave originating from the antenna reaches the cradle device, a surface current is induced. That current will in turn generate a responsive electromagnetic field that will interfere with the incident field in such a way that the total electromagnetic field in the cradle device will be negligible.

While a majority of the electromagnetic energy is reflected by the metallic cradle device 26, since it is not a perfect conductor, a fraction of the incident electromagnetic energy is absorbed by resistive losses therein. Consequently, the cradle device 26 itself may eventually generate heat in an amount detrimental to the surrounding tissue. The shield assembly 25 of the present invention, therefore, preferably includes an insulator 52 disposed about the cradle device 26 to insulate the surrounding tissues from the cradle device. As best viewed in FIGS. 2–4, insulator 52 is disposed peripherally about the cradle device 26 in a manner conductively contacting the outer surface thereof and particularly substantially along its length dimension.

The insulator 52 provides a longitudinally extending bore 53 formed and dimensioned for sliding receipt of the cradle device 26 therein. Preferably, such sliding receipt is performed through an interference fit to insure conductive contact between the insulator and the cradle device. Accordingly, the insulator 52 further performs the function, in part, of a heat sink for the transfer and dissipation of heat into the insulator 52 from the cradle device 26.

Similar to the insert device 42, the insulator 52 defines a directional window 55 extending into the bore 53 from a side wall thereof. This directional window 55 is aligned to communicate with the window portion 27 of the cradle device 26 and the directional port 45 of the insert device 42 so that the cradle device can direct the majority of the field generally in the predetermined direction. Preferably, as viewed in FIG. 4, the directional window 55 of the insulator 52 is circumferentially dimensioned slightly smaller than or substantially equal to the circumferential dimension of the window portion 27 of cradle device 26. This arrangement minimized exposure of the edges defining the window portion 27 to tissues during operation.

To appropriately cool the cradle device during operational use, the insulator 52 must be designed with a sufficient heat transfer capacity to transfer and dissipate the heat continuously generated by the cradle device. One factor determining both the insulatory and heat sink capacity is the material composition. The insulator material, however, preferably has a low loss-tangent and low water absorption so that it is not itself heated by the microwaves. In accordance with the present invention, the insulator is preferably provided by a suitable thermoplastic material such as ABS plastic.

The other primary factor determining the heat sink capacity is the volume of the insulator contacting the cradle device. FIGS. 3 and 4 best illustrate that the insulator 52 is preferably substantially cylindrical-shaped in conformance with the peripheral dimensions of the cradle device 26. The longitudinal axis of bore 53 is off-set from that of the insulator 52 which functions to position the antenna 23 in the aligned windows, and collectively closer to tissues targeted for ablation. Moreover, a backside of the insulator 52 is substantially thicker and more voluminous than the opposed frontside thereof which defines the directional window 55. This configuration provides greater heat sink capacity at the backside of the insulator 52 which conductively contacts a substantial majority of the backside of cradle device 26.

Bore 53 preferably includes a distal opening 58 therein which is formed for sliding receipt of the substantially uniform transverse cross-sectional dimension of the cradle device 26. Sliding support of the insulator 52 longitudinally along the cradle device 26 continues until a back wall 56 of the bore 53 contacts the proximal edge 57 of the cradle device 26. This functions to limit the insertion of the cradle device 26 in the bore 53. At the distal end portion of the insulator 52, the annular shoulder portion 50 of the insert device 42 slideably contacts the interior wall of the bore distal opening 58 to secure the insulator to the cradle device and the insert device. The circumferential dimension of the shoulder portion 50 is preferably dimensioned to provide an interference fit with the shoulder portion. Thus, the outer diameter of the shoulder portion 50 is preferably slightly larger than the inner diameter of the bore 53 of the insulator 52. An adhesive, such as cyanoacrylate, may be applied to further secure the insulator in place.

As shown in FIGS. 2 and 3, once the insulator is properly positioned, the distal end thereof is dimensioned to be positioned substantially flush with the distal end of the insert device 42. Further, the insert device 42 and the insulator 52 cooperate to enclose the distal edge 51-of the cradle device therein.

Figure 6:
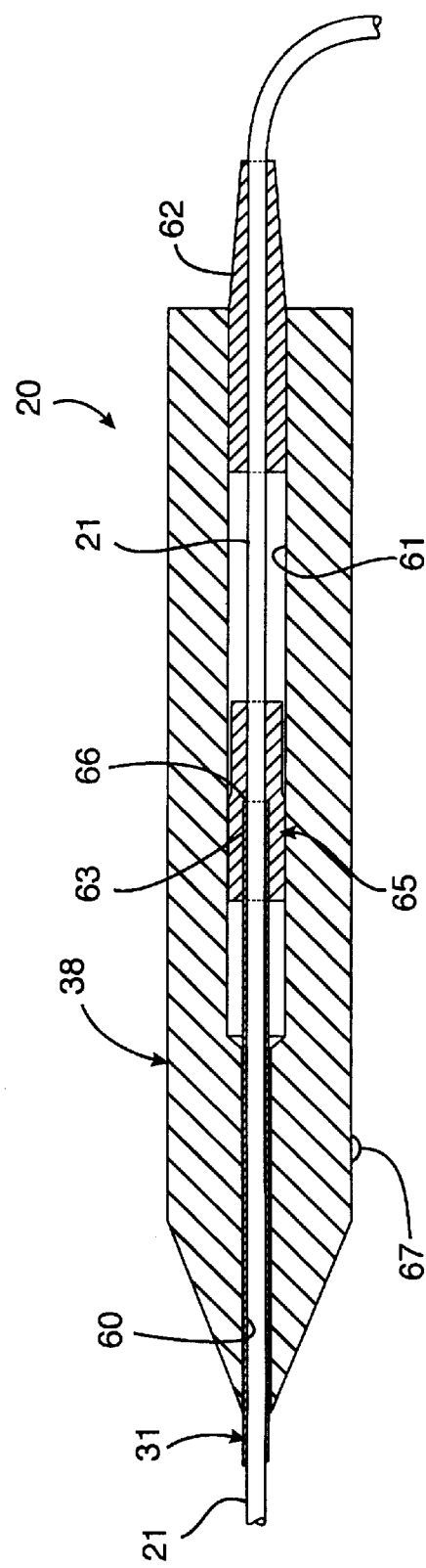
FIG. 6 is a fragmentary, side elevation view, in cross-section, of a handle of the ablation instrument system of the present invention.

Referring now to FIG. 6, a handle 38 for the ablation instrument 20 will be described in detail. In the preferred form, the handle 38 is composed of a nonconductive, relatively rigid material, such as ABS plastic. As above indicated, the handle 38 is provided as a vehicle to manually manipulate the orientation and positioning of the cradle window portion 27 during operational use. This is performed by rigidly attaching the handle to a proximal end portion of the shaft 31.

At a distal portion of the handle 38, a passage 60 extends axially into an interior portion of the handle. The diameter of the passage 60 is preferably substantially equal to the shaft diameter to minimize the tolerance therebetween. An interior wall 61 of the handle portion defines an axially extending cavity 36 which communicates with the distal passage 60. The cavity 36 is preferably of a diameter larger than that of the passage 60, and preferably extends through handle 38 substantially coaxial with the passage 60.

The shaft is positioned in the handle passage 60 such that the shaft proximal end terminates in the cavity 36. To rigidly mount the shaft 31 to the handle 38, an insert screw (not shown) or the like, or an adhesive may be applied in the passage between the shaft 31 and the handle 38.

As shown in FIG. 6, the transmission line 21 extends through the proximal cavity 36 and into the tubular shaft for coupling to the antenna 23. An elastic retraining device 62 may be provided mounted in the cavity 36 at the proximal end of the handle which cooperates with the transmission line 21 to mount the same to the handle.

Due to the conductive nature of the metallic hypotube or tubular shaft 31 and the coaxial arrangement between outer conductor of the coaxial cable and the metallic shaft, a second transmission line is formed between these substantially concentric cylindrical metallic surfaces. Electromagnetic energy emitted by the antenna excites this second transmission line which detrimentally propagates microwave energy between metallic tube and the outer conductor of the coaxial cable. Thus, a part of the microwave energy is propagated back toward the handle.

In accordance with the present invention, handle 38 further includes a microwave absorbent 65 disposed peripherally around the proximal portion of the tubular shaft 31 to substantially absorb microwave radiation transmitted by the proximal end thereof. While the microwave absorbent may be integrally formed in the materials composing the handle, it is preferred that a material 65 containing the microwave absorbent be disposed or wrapped about the juncture 66 between proximal end 63 of the shaft 31 and transmission line 21, as shown in FIG. 6.

In the preferred embodiment, this material wrap 65 is a silicon based microwave absorbent, such as C-RAM KRS-124 from Cuming Microwave Corp. having a thickness of about 0.085 inches. Moreover, this material wrap 65 must be sufficient in length to extend over the juncture 66 between the shaft proximal end 63 and the transmission line 21. Preferably, the wrap extends equidistant from the juncture 66 in each direction by about 0.25 inches to about 0.75 inches. This distance may vary depending upon the anticipated amount of electromagnetic field transmission, the material thickness and the type of microwave absorbent applied.

In accordance with the present invention, to facilitate location of the window portion 27 relative the handle 38 during operative use, a marking device 67 and method are provided. Such location marking is particularly useful during operative use when the antenna and shield assembly cannot be easily viewed.

Preferably, a visual or tactile marking device 67 (FIG. 6) is located along the handle 38 to communicate to the surgeon the location and orientation window portion. This visual marking may be provided by a simple depression mark, painted mark or illuminated mark, or the like easily viewed along the handle. This marking is preferably positioned and aligned in a plane bisecting the window portion 27 and the handle 38. More preferably, as shown in FIG. 6, the marking is positioned on the same side of the handle as the window portion 27. However, it will be understood that the marking may be placed anywhere along the handle 38 as long as the position thereof remains affixed relative the window portion.

Although only a few embodiments of the present inventions have been described in detail, it should be understood that the present inventions may be embodied in many other specific forms without departing from the spirit or scope of the inventions. Particularly, the invention has been described in terms of a microwave ablation instrument for cardiac applications, however, it should be appreciated that the described small diameter microwave ablation instrument could be used for a wide variety of non-cardiac ablation applications as well. The size and pitch of the described antenna coils may be widely varied. It should also be appreciated that the longitudinally oriented antenna coil does not need to be strictly parallel relative to the shaft axis and indeed, in some embodiments it may be desirable to tilt the antenna coil somewhat. This is especially true when the malleable shaft is reconfigured to the particular needs of the surgical application.

It should also be appreciated that the microwave antenna need not be helical in design. The concepts of the present invention may be applied to any kind of radiative structure, such as a monopole antenna, a printed antenna, a slow wave antenna, a lossy transmission antenna or the like. Furthermore, it should be appreciated that the transmission line does not absolutely have to be a coaxial cable. For example, the transmission line may be provided by a stripline, a microstrip line, a coplanar line, or the like.

What is claimed is:

1. A microwave ablation instrument comprising:
   a transmission line having a proximal portion suitable for connection to an electromagnetic energy source;
   an antenna, having a longitudinal axis, coupled to the transmission line for radially generating an electric field sufficiently strong to cause tissue ablation; and
   a shield assembly having a central axis and a window portion, and coupled to said antenna to substantially shield a surrounding area of the antenna from the electric field radially generated therefrom while permitting a majority of the field to be directed out of the window portion thereof generally in a predetermined direction, wherein, said longitudinal axis of said antenna is off-set from the central axis of said shield assembly to position said antenna substantially proximate to and adjacent said window portion.

2. The microwave ablation instrument according to claim 1 wherein, said shield assembly includes a cradle device disposed about the antenna for substantial shielding of the antenna surrounding area, said cradle device defining said window portion communicating with said antenna and strategically located therewith to direct the majority of the field generally in the predetermined direction.

3. The microwave ablation instrument according to claim 2 wherein, said cradle device is adapted to position said antenna proximate to and adjacent said window portion.

4. The microwave ablation instrument according to claim 3 wherein, said cradle device defines a cavity in communication with said window portion, and formed and dimensioned for receipt of the antenna therein.

5. The microwave ablation instrument according to claim 4 further including:

an insert device disposed in said cavity and defining a recess formed and dimensioned for receipt of said antenna therein in a manner substantially isolating said antenna from direct contact with the metallic cradle device.

6. The microwave ablation instrument according to claim 5 wherein, said insert device defines a directional port extending into said recess and aligned to communicate with the window portion of said cradle device to direct said majority of the field generally in said predetermined direction.

7. The microwave ablation instrument according to claim 6 wherein, said cavity is generally elongated, and formed for longitudinal receipt of said antenna therein.

8. The microwave ablation instrument according to claim 7 wherein, a longitudinal axis of said elongated recess is off-set from a longitudinal axis of said cradle to positioned to position said antenna substantially proximate to and adjacent said directional port and said window portion.

9. The microwave ablation instrument according to claim 6 further including:

an insulator in conductive contact with said cradle device to transfer heat therefrom.

10. The microwave ablation instrument according to claim 9 wherein, said insulator includes a longitudinally extending bore formed and dimensioned for sliding receipt of said cradle device therein.

11. The microwave ablation instrument according to claim 10 wherein, said insulator defines a directional window extending into said bore and aligned to communicate with the window portion of said cradle device to direct said majority of the field generally in said predetermined direction.

12. The microwave ablation instrument according to claim 2 further including:

a conductive, bendable, malleable tubular shaft having a proximal portion and a distal portion coupled to said cradle device, said transmission line being disposed in said tubular shaft from the proximal portion to the distal portion thereof.

13. The microwave ablation instrument according to claim 12 further including:

a handle mounted to the proximal portion of said tubular shaft.

14. The microwave ablation instrument according to claim 13 wherein, said handle includes a microwave absorbent disposed peripherally around the proximal portion of said tubular shaft to substantially absorb microwave radiation transmitted by the proximal portion.

15. The microwave ablation instrument according to claim 14 wherein, said microwave absorbent is provided by a silicon based microwave absorbent.

16. The microwave ablation instrument according to claim 14 wherein, said handle includes an interior wall defining a cavity portion formed and dimensioned for termination of the tubular shaft proximal portion terminates therein, and said ablation instrument further including:

a material containing said microwave absorbent disposed about said proximal portion and said transmission line in said cavity.

17. The microwave ablation instrument according to claim 1 wherein:

said antenna is provided by a helical antenna coil that is adapted to radiate electromagnetic energy in the microwave frequency range.

18. The microwave ablation instrument according to claim 17 wherein:

the transmission line is a coaxial transmission line suitable for transmission of microwave energy at frequencies in the range of approximately 800 to 6000 megahertz, the coaxial transmission line having a center conductor, a shield and a dielectric material disposed between the center conductor and shield.

19. A microwave ablation instrument comprising:

a conductive, bendable, malleable tubular shaft having a proximal portion and a distal portion;

a transmission line disposed within the tubular shaft, and having a proximal portion suitable for connection to an electromagnetic energy source;

an antenna supported by the distal portion of said tubular shaft, and coupled to the transmission line for radially generating an electric field sufficiently strong to cause tissue ablation; and a microwave absorbent disposed peripherally around the proximal portion of said tubular shaft to substantially absorb residual microwave radiation transmitted by the proximal portion thereof.

20. The microwave ablation instrument according to claim 19 further including:

a handle mounted to the proximal portion of said tubular shaft.

21. The microwave ablation instrument according to claim 20 wherein, said microwave absorbent is integrally formed with said handle.

22. The microwave ablation instrument according to claim 19 wherein, said microwave absorbent is provided by a silicon based microwave absorbent.

23. The microwave ablation instrument according to claim 20 wherein, said handle includes an interior wall defining a cavity portion formed and dimensioned for termination of the tubular shaft proximal portion terminates therein.

24. The microwave ablation instrument according to claim 23 further including:

a material containing said microwave absorbent disposed about said proximal portion and said transmission line in said cavity.

25. The microwave ablation instrument according to claim 24 wherein:

the transmission line is a coaxial transmission line suitable for transmission of microwave energy at frequencies in the range of approximately 800 to 6000 megahertz, the coaxial transmission line having a center conductor, a shield and a dielectric material disposed between the center conductor and shield.

26. A microwave ablation instrument adapted to ablate tissue comprising:

a transmission line having a proximal portion suitable for connection to an electromagnetic energy source;

an antenna, having a longitudinal axis, coupled to the transmission line for radially generating an electric field sufficiently strong to cause tissue ablation; and a shield assembly having a central axis and coupled to said antenna to substantially shield a surrounding area of the antenna from the electric field radially generated therefrom, wherein said longitudinal axis of said antenna is off-set from the central axis of said shield assembly.

27. The microwave ablation instrument according to claim 26 wherein, said off-set of the antenna longitudinal axis is in a direction away from the shield assembly.

28. The microwave ablation instrument according to claim 27 wherein, said shield assembly is configured to cooperate with said antenna to direct a majority of the electric field generated by said antenna out of a window portion thereof.

29. The microwave ablation instrument according to claim 27 wherein, said off-set of the antenna longitudinal axis positions said antenna in said window portion in a manner substantially proximate to and adjacent the tissue targeted for ablations.

* * * * *